US009200190B2

(12) United States Patent
Maxey et al.

(10) Patent No.: US 9,200,190 B2
(45) Date of Patent: Dec. 1, 2015

(54) METHODS RELATING TO PREDICTING SUBTERRANEAN FORMATION DAMAGE FROM DEFORMABLE ADDITIVES

(75) Inventors: Jason Eric Maxey, Spring, TX (US); Ryan Matthew Van Zanten, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 54 days.

(21) Appl. No.: 13/372,294

(22) Filed: Feb. 13, 2012

(65) Prior Publication Data

US 2013/0205874 A1 Aug. 15, 2013

(51) Int. Cl.
*C09K 8/00* (2006.01)
*G01N 3/12* (2006.01)
*G01N 15/08* (2006.01)

(52) U.S. Cl.
CPC .. *C09K 8/00* (2013.01); *G01N 3/12* (2013.01); *G01N 15/08* (2013.01); *G01N 2203/0025* (2013.01); *G01N 2203/0284* (2013.01)

(58) Field of Classification Search
USPC ........................................ 73/54.39
See application file for complete search history.

(56) References Cited

U.S. PATENT DOCUMENTS

| 4,960,821 | A | 10/1990 | Peiffer |
| 5,036,136 | A | 7/1991 | Peiffer |
| 5,905,061 | A | 5/1999 | Patel |
| 5,977,031 | A | 11/1999 | Patel |
| 6,828,279 | B2 | 12/2004 | Patel et al. |
| 7,534,745 | B2 | 5/2009 | Taylor et al. |
| 7,645,723 | B2 | 1/2010 | Kirsner et al. |
| 7,696,131 | B2 * | 4/2010 | Oyler et al. ............... 507/103 |
| 2007/0184987 | A1 * | 8/2007 | Brandbury et al. ......... 507/140 |
| 2008/0047709 | A1 | 2/2008 | Tremblay et al. |
| 2008/0060811 | A1 | 3/2008 | Bour et al. |
| 2010/0181070 | A1 * | 7/2010 | Harris et al. ............... 166/280.1 |
| 2012/0024530 | A1 | 2/2012 | Todd et al. |

FOREIGN PATENT DOCUMENTS

WO 2013122772 A1 8/2013

OTHER PUBLICATIONS

M. Pancharoen, Physical Properties of Associative Polymer Solutions, Jun. 2009.*
International Search Report and Written Opinion for PCT/US2013/024715 dated Apr. 18, 2013.
Kwan et al., "An Experimental and Simulation Study of Dilute Polymer Solutions in Exponential Shear Flow: Comparison to Uniaxial and Planar Extensional Flows," The Society of Rheology, Inc., 2001.

(Continued)

*Primary Examiner* — Daniel S Larkin
*Assistant Examiner* — Irving A Campbell
(74) *Attorney, Agent, or Firm* — McDermott Will & Emery LLP; Holly Soehnge

(57) ABSTRACT

Predicting subterranean formation damages from deformable additives in treatment fluids may include measuring exponential shear values for samples comprising a base fluid and at least one deformable additive. Then the relative pore plugging propensity of the deformable additives may be determined by comparing the exponential shear values or rheological values derived therefrom from either two or more deformable additives to each other or from one or more deformable additives to a pore plugging propensity scale.

8 Claims, 7 Drawing Sheets

(56) References Cited

OTHER PUBLICATIONS

Zulle et al., "Deformation Hardening and Thinning in Both Elongation and Shear of a Low Density Polyethylene Melt," Institut for Polymere, Eidgenossiche Technische Hochschule,1987.
Doshi et al., "Exponential Shear: A Strong Flow," Department of Chemical Engineering, McGill University, 1987.
Wagner et al., "Exponential Shear Flow of Branched Polyethylenes in Rotational Parallel-Plate Geometry," Rheol Acta, 2005, 45: 164-173.
Venerus, David C., "Exponential Shear Flow of Branched Polymer Melts," Rheol Acta, 2000, 39: 71-79.
Neergaard et al., "Exponential Shear Flow of Linear, Entangled Polymeric Liquids," The Society of Rheology, Inc., 2000.
Dealy et al., "Interrupted Shear," Structure and Rheology of Molten Polymers, 2006.
Demarquette et al., "Nonlinear Viscoelasticity of Concentrated Polystyrene Solutions: Sliding Plate Rheometer Studies," The Society of Rheology, Inc., 1992.
Samurkas et al., "Strong Extensional and Shearing Flows of a Branched Polyethylene," The Society of Rheology, Inc. Journal of Rheology, 33(4), 559-578, 1989.
08_Plasticity_06_Hardening—ref: <http://homepages.engineering.auckland.ac.nz/~pkel015/SolidMechanicsBooks/Part_II/index.html>, lecture notes online book from U. Aukland, Solid Mechanics Part II, not dated.
Liu et al., Studying the Origin of "Strain Hardening": Basic Difference Between Extension and Shear, The Society of Rheology, Inc., 2013, J. Rheol. 57(1), 89-104.
Zulle et al., Deformation Hardening and Thinning in Both Elongation and Shear of a Low Density Polyethylene Melt, The Society of Rheology, Inc., Journal of Rheology, 31 (7), 583-598, 1987.
Dealy J.M., Do Polymeric Liquids Exhibit Strain Hardening?, The Society of Rheology, Inc., J. Rheol 34(7), Oct. 1990.

* cited by examiner

METHODS RELATING TO PREDICTING SUBTERRANEAN FORMATION DAMAGE FROM DEFORMABLE ADDITIVES

BACKGROUND

The present invention relates to predicting subterranean formation damage caused by deformable additives present in treatment fluids and related compositions and methods.

Exploration and production of subterranean fluids often involves placing treatment fluids into the subterranean formation for various purposes. The treatment fluids in subterranean formations may include deformable additives, i.e., having a morphology that deforms. As used herein, the term "treatment," or "treating," refers to any subterranean operation that uses a fluid in conjunction with a desired function and/or for a desired purpose, e.g., drilling, stimulation, sand control, fracturing, wellbore strengthening, fluid loss control, and completion operations. The term "treatment," or "treating," does not imply any particular action by the fluid.

Depending on the nature of the subterranean formation, deformable additives may lead to formation damage that can be costly and time consuming to repair. For example, subterranean formations with low porosity may be susceptible to pore plugging when deformable additives are employed. As a deformable additive passes through a pore, the additive and fluid will experience extensional flows through the pore. During extrusion the deformable additive may deform into an elongated morphology, which can be a highly strained conformation that becomes substantially immobile, and therefore plugs the pore.

Three primary avenues to removing the additive now having an elongated morphology from a pore may include allowing the structure to relax into a less strained conformation, applying a high back-pressure to push the additive out, and degrading the additive into smaller components that are more easily removed from the pore. Each of these methods are time-consuming, however, and potentially costly, and bring with them the potential for further damage, e.g., acidizing to degrade a gelling agent may remove the gelling agent but can also cause undesirable damage to the faces of the formation.

Alternatively, the subterranean formation may be fractured to return at least some of the permeability. This avenue may not address the underlying problem of pore plugging, however, because it creates new fractures and pores for formation fluids to flow rather than ameliorating the plugging.

To mitigate the potential of formation damage from deformable additives, return permeability tests can be performed. Return permeability tests often involve a multistage process that can take up to two-days and cost tens of thousands of dollars to test a single treatment fluid having a deformable additive, in addition to the rig down-time. Further, return permeability tests typically involve core samples, which can be inconsistent and introduce a high degree of uncertainty into the testing.

Methods that are faster and less costly for the prediction of formation damage from treatment fluids having a deformable additive may be of value to one skilled in the art.

SUMMARY OF THE INVENTION

The present invention relates to predicting subterranean formation damages caused by deformable additives present in treatment fluids and related compositions and methods.

Some embodiments of the present invention provide for a method that includes measuring exponential shear values of two or more samples each comprising a base fluid and at least one deformable additive, and determining a relative pore plugging propensity of the samples relative to each other from the exponential shear values or rheological values derived therefrom.

Some embodiments of the present invention provide for a method that includes measuring exponential shear values of at least two samples, determining a relative pore plugging propensity of the samples relative to each other from the exponential shear values or rheological values derived therefrom, and formulating a treatment fluid based on the relative pore plugging propensity of the samples relative to each. The samples each having a base fluid and at least one deformable additive, wherein the deformable additive composition of each sample is different.

Some embodiments of the present invention provide for a method that includes measuring a strain hardening value for a sample under exponential shear with a strain scale factor of 0.5, the sample including a base fluid and at least one deformable additive, and developing a treatment fluid additive based on the strain hardening value relative to a strain hardening scale.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
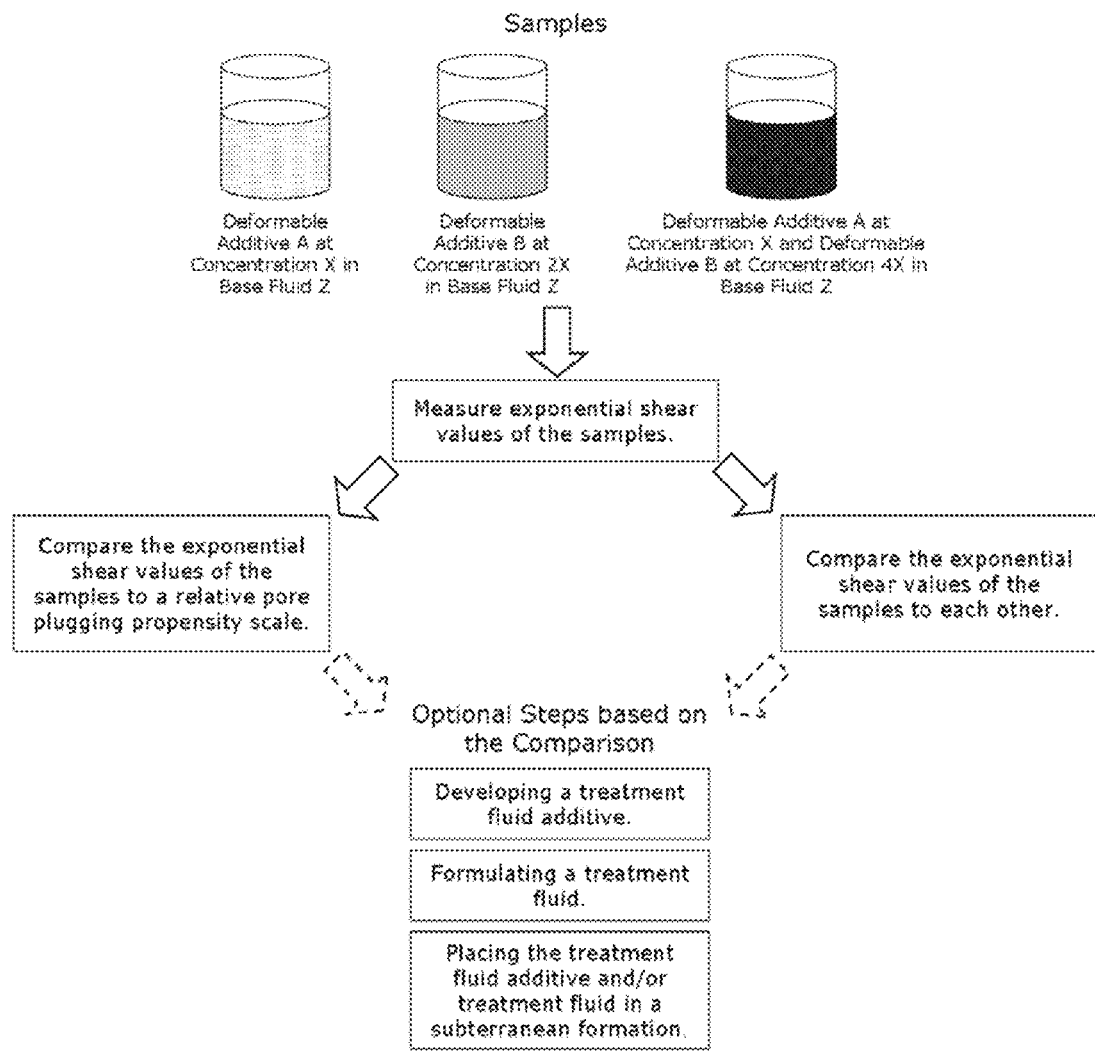
FIG. 1 provides a flow chart of a nonlimiting example a method of the present invention.

The present invention relates to predicting subterranean formation damages caused by deformable additives present in treatment fluids and related compositions and methods.

The present invention provides, in some embodiments, methods for determining the relative pore plugging propensity of deformable additives (e.g., polymers and emulsion droplets) based on the rheological properties of one or more fluids containing such additives. The methods are useful for developing treatment fluids with deformable additives having a minimized potential to plug the porosity of a subterranean formation, thereby reducing the cost and rig down-time due to damaged formations. As described herein, relativity as it relates to pore plugging propensity refers to both two or more deformable additives as compared to each other and to one or more deformable additives as compared to a pore plugging propensity scale. As used herein, the term "deformable additive," and derivatives thereof, refers to an additive having a morphology that deforms with the application of external pressures from fluid flow, e.g., shear stress, normal stress, and extrusion. It should be noted that deformation by external pressure from fluid flow does not include the degradation (e.g., hydrolysis, chain fracture, etc.) of the additive. As used herein, the term "sample" refers generally to the sample for which exponential shear values may be measured in the determination of the relative pore plugging propensity.

Because the methods of the present invention involve rheological characterization and methods, the methods may be advantageously fast and low-cost relative to known return permeability tests, described above. For example, methods of the present invention may, in some embodiments, take hours rather than days and cost at least one-tenth that of known return permeability tests.

In some embodiments, the methods of the present invention may be used to develop treatment fluids that minimize pore plugging or that maximize pore plugging within a desired zone in a subterranean formation, depending on the desired effect. Increasing or decreasing pore plugging may depend on the particular zone of interest within a subterranean formation and its inherent porosity. For example, in a production zone, it may be desirable to decrease pore plugging, whereas in a drilling zone, it may be more desirable to increase pore plugging. Additionally, treatment fluids with minimal pore plugging potential may advantageously be used in subterranean operations where porosity maintenance is desired (e.g., drilling, acidizing, and fracturing operations). The term "porosity maintenance" as used herein refers to the maintenance of the current porosity of the formation within tolerable limitations. By way of nonlimiting example, in fracturing operation it may be desirable to create fractures while maintaining the porosity of the formation proximal to the fractures so as to allow formation fluids to flow from the formation into the fractures. Treatment fluids with a higher pore plugging potential may advantageously be used in subterranean operations where pore plugging is desired (e.g., fluid loss control, wellbore strengthening, and zonal isolation operations).

FIG. 1 provides a nonlimiting example of a method of the present invention with three samples that contain (1) deformable additive A at concentration X in base fluid Z, (2) deformable additive B at concentration 2X in base fluid Z, and (3) deformable additive A at concentration X and deformable additive B at concentration 4X in base fluid Z. The exponential shear values are measured for each sample, which can be compared to each other and/or to a relative pore plugging propensity scale (described further herein). Then optionally, a treatment fluid additive and/or treatment fluid can be developed based on the comparison of the relative pore plugging propensity of the samples. Development of the treatment fluid additive and/or treatment fluid are described further herein. Further, the treatment fluid additive and/or treatment fluid may be introduced into a subterranean formation for a variety of operations, described in further detail herein.

It should be noted that when "about" is provided at the beginning of a numerical list, "about" modifies each number of the numerical list. It should be noted that in some numerical listings of ranges, some lower limits listed may be greater than some upper limits listed. One skilled in the art will recognize that the selected subset will require the selection of an upper limit in excess of the selected lower limit. Whenever a range of values is given, any subset of that range (between the highest and lowest point) is an acceptable alternative range in the embodiments of the present invention.

Some embodiments of the present invention may involve determining the relative pore plugging propensity of one or more samples. In some embodiments, samples for use in conjunction with the present invention may comprise a base fluid and at least one deformable additive. In some embodiments, samples for use in conjunction with the present invention may comprise a base fluid, at least one deformable additive, and at least one additional additive. It should be noted that, in some embodiments, it may be undesirable to include additional additives in the samples as the additional additives may mask the exponential shear values of the deformable additives being tested.

In some embodiments when two or more samples are compared to each other, samples for use in conjunction with the present invention may have different compositions, e.g., different deformable additives, different concentrations of the same deformable additives, different relative concentrations of two or more deformable additives, different base fluids, different additional additives, different concentrations of the same additional additives, different relative concentrations of two or more additional additives, or any combination thereof. By way of nonlimiting example, a first sample may comprise a first base fluid and a first deformable additive, and a second sample may comprise the first base fluid and a second deformable additive. By way of another nonlimiting example, a first sample may comprise a first base fluid and a first deformable additive, and a second sample may comprise the first base fluid, the first deformable additive, and a second deformable additive. By way of another nonlimiting example, a first sample may comprise a first base fluid and a first deformable additive, and a second sample may comprise a second base fluid and the first deformable additive. By way of another nonlimiting example, a first sample may comprise a first base fluid and a first deformable additive, and a second sample may comprise a second base fluid and a second deformable additive, where the first and second base fluids may be substantially similar, e.g., brines with different compositions.

It should be noted that comparisons between two or more samples or between one or more samples and a pore plugging propensity scale may be done by a person, a computer, or any combination thereof.

As described above, deformable additives are generally additives having a morphology that deforms with the application of external pressures from fluid flow, e.g., shear stress, normal stress, and extrusion. Nonlimiting examples of deformable additives may include polymers, gelling agents, viscoelastic surfactants, emulsion droplets, liquid crystals, polymeric microgels, capsules, deformable weighting agents, plasticized polymeric additives, lost circulation materials, fibers, carbon nanotubes, and any combination thereof. Further, hard particles that have deformable coatings and/or surface treatments are considered deformable additives, as used herein. An example includes gravel particulates that have a coating of plasticized poly(lactic acid). It should be recognized by one skilled in the art with the benefit of this disclosure that deformability may be temperature dependent, and therefore, the conditions present in the particular subterranean application may render an additive deformable.

Suitable concentrations of deformable additives in samples for use in conjunction with the present invention may be any concentration comparable to a concentration suitable for use in subterranean formations. In some embodiments, the concentration of deformable additives in samples for use in conjunction with the present invention may range from about 0.001%, 0.01%, 0.05%, 0.1%, 1%, 5%, 10%, or 25% by volume of the base fluid to an upper limit of about 75%, 50%, 25%, or 10% by volume of the base fluid, and wherein the concentration of the deformable additive may range from any lower limit to any upper limit and encompasses any subset therebetween.

Suitable base fluids for use in conjunction with the present invention may include, but not be limited to, oil-based fluids, aqueous-based fluids, aqueous-miscible fluids, water-in-oil emulsions, or oil-in-water emulsions. Suitable oil-based fluids may include alkanes, olefins, aromatic organic compounds, cyclic alkanes, paraffins, diesel fluids, mineral oils, desulfurized hydrogenated kerosenes, and any combination thereof. Suitable aqueous-based fluids may include fresh water, saltwater (e.g., water containing one or more salts dissolved therein), brine (e.g., saturated salt water), seawater, and any combination thereof. Suitable aqueous-miscible fluids may include, but not be limited to, alcohols, e.g., methanol, ethanol, n-propanol, isopropanol, n-butanol, sec-butanol, isobutanol, and t-butanol; glycerins; glycols, e.g., polyglycols, propylene glycol, and ethylene glycol; polyglycol amines; polyols; any derivative thereof; any in combination with salts, e.g., sodium chloride, calcium chloride, calcium bromide, zinc bromide, potassium carbonate, sodium formate, potassium formate, cesium formate, sodium acetate, potassium acetate, calcium acetate, ammonium acetate, ammonium chloride, ammonium bromide, sodium nitrate, potassium nitrate, ammonium nitrate, ammonium sulfate, calcium nitrate, sodium carbonate, and potassium carbonate; any in combination with an aqueous-based fluid; and any combination thereof. Suitable water-in-oil emulsions, also known as invert emulsions, may have an oil-to-water ratio from a lower limit of greater than about 50:50, 55:45, 60:40, 65:35, 70:30, 75:25, or 80:20 to an upper limit of less than about 100:0, 95:5, 90:10, 85:15, 80:20, 75:25, 70:30, or 65:35 by volume in the base fluid, where the amount may range from any lower limit to any upper limit and encompass any subset therebetween. Examples of suitable invert emulsions include those disclosed in U.S. Pat. Nos. 5,905,061, 5,977,031, 6,828,279, 7,534,745, 7,645,723, and 7,696,131, each of which are incorporated herein by reference. It should be noted that for water-in-oil and oil-in-water emulsions, any mixture of the above may be used including the water being and/or comprising an aqueous-miscible fluid.

As used herein, the term additional additives refers to treatment fluid additives not being deformable additives. Suitable additional additives may include, but are not limited to, salts, weighting agents, inert solids, fluid loss control agents, emulsifiers, dispersion aids, corrosion inhibitors, emulsion thinners, emulsion thickeners, surfactants, particulates, proppants, gravel particulates, lost circulation materials, foaming agents, gases, pH control additives, breakers, biocides, crosslinkers, stabilizers, chelating agents, scale inhibitors, gas hydrate inhibitors, mutual solvents, oxidizers, reducers, friction reducers, clay stabilizing agents, and any combination thereof. Suitable concentrations of additional additives in samples for use in conjunction with the present invention may be any concentration comparable to a concentration suitable for use in subterranean formations, e.g., depending on the treatment fluid of interest an additive may be included up to about 25% by volume of the treatment fluid.

In some embodiments, determining the relative pore plugging propensity of deformable additives may involve measuring exponential shear values of samples comprising the deformable additives. As used herein, the exponential shear value refers to one of several properties measured under exponentially increasing shear, which may be related to the ability of a fluid and deformable additive to invade in the zone within a subterranean formation.

Some embodiments of the present invention may involve comparing the exponential shear values or rheological values derived therefrom to determine the relative pore plugging propensity of the deformable additives. Determination of a relative pore plugging propensity may be achieved through, in some embodiments, comparison of two or more samples, comparison of one or more samples to a relative pore plugging propensity scale (described further herein), or any combination thereof. It should be noted that when comparing samples to each other or a scale, one skilled in the art with the benefit of this disclosure should recognize that the most accurate relative pore plugging propensities may be when comparing samples with base fluids of similar composition, e.g., comparisons of aqueous-based fluids and oil-based fluids may not be as accurate as comparisons between aqueous-based fluids or between oil-based fluids.

Suitable rheological values derived from exponential shear values may include, but are not limited to, strain hardening, strain softening, shear thinning, an extensional viscosity measure, or any combination thereof. One skilled in the art with the benefit of this disclosure should understand that the exponential shear values or rheological values derived therefrom may be measured by a plurality of methods. By way of non-limiting example, a method may include using a rheometer, e.g., an MCR-501 available from Anton-Paar, with 50 mm diameter parallel plates. After a sample is placed and heated to the appropriate temperature, e.g., 120° F., the software of the instrument can be programmed to run the rheometer with exponentially increasing shear rates and measure the exponential shear values.

Exponential shear ($\gamma(t)$) may be expressed as Formula I, below, where A is the strain scale factor, $\alpha$ is the exponential rate constant, $\gamma$ is the strain, and t is time. For a series of constant $\alpha$, increasing A will result in increasing maximum strain experienced. If A is held constant, increasing $\alpha$ will increase the acceleration of the shear rate through the test.

$$\gamma(t)=A(e^{\alpha t}-1) \qquad \text{Formula I}$$

As used herein, the term "strain hardening" refers to the increase in stress required to produce additional strain in the fluid. This may depend on the constant $\alpha$. For example, at a fixed exponential acceleration rate ($\alpha$) a lower strain at which a positive inflection in the exponential viscosity curve occurs may indicate a lower propensity for formation damage. Strain hardening may lead to decreased ability for the deformable material to penetrate the porous media, leading to less formation damage or poorer wellbore strengthening (less pore plugging propensity). In some embodiments of the present invention, the relative pore plugging propensity may be higher for deformable additives exhibiting lower to no strain hardening.

In some embodiments, the relative pore plugging propensity for a deformable additive may be related to a strain hardening scale. One skilled in the art with the benefit of this disclosure should understand that the strain hardening scale will depend on the $\alpha$ used for the strain hardening methods. By way of nonlimiting example, a strain hardening scale with $\alpha=0.5$ may be high relative pore plugging propensity for samples that exhibit strain hardening at a strain of about 500 or greater, medium relative pore plugging propensity for samples that exhibit strain hardening at a strain of about 200 to about 500, low relative pore plugging propensity for samples that exhibit strain hardening at a strain of about 5 to about 200, and minimal relative pore plugging propensity for samples that exhibit no strain hardening to a strain hardening at a strain of about 5.

As used herein, the term "strain softening" refers to the decrease in stress required to produce additional strain in the fluid. Strain softening may lead to increased ability for the deformable material to penetrate the porous media, and thus, lead to more formation damage or better wellbore strengthening (increased pore plugging propensity). In some embodiments of the present invention, the relative pore plugging propensity may be higher for deformable additives exhibiting strain softening.

As used herein, the term "shear thinning" refers to the decrease in shear viscosity or principal exponential stress growth coefficient (principal exponential viscosity) with increased shear rate. In some embodiments of the present invention, the relative pore plugging propensity may be lower for deformable additives exhibiting substantially consistent shear thinning of the principal exponential viscosity over shear rates ranging from about $10^{-1}$ $s^{-1}$ to about $10^3$ $s^{-1}$. By way of a nonlimiting example, deformable additives may have a higher pore plugging propensity when exhibiting shear thinning of the principal exponential viscosity with a dip at higher shear rates (e.g., at about $10^1$ $s^{-1}$ to about $10^2$ $s^{-1}$) followed by a region of shear thickening at still higher shear rates (e.g., above about $10^2$ $s^{-1}$).

As used herein, the term "extensional viscosity measure" refers to an indication of the degree of extensional viscosity, i.e., the coefficient of the change in stress due to extension with increased extensional flow, and should not be taken to be an absolute measurement of extensional viscosity. In some embodiments of the present invention, the relative pore plugging propensity may be higher for deformable additives having a higher extensional viscosity.

Some embodiments of the present invention may involve developing and/or formulating treatment fluids or treatment fluid additives based on the relative pore plugging propensity of samples used in conjunction with the present invention, whether the relative pore plugging propensity be based on two or more samples relative to each other or one or more samples relative to a scale. Suitable treatment fluid and/or treatment fluid additive parameters that are based on the relative pore plugging propensity samples tested may include, but are not limited to, the concentration or range of concentration of one or more deformable additives, the composition of one or more deformable additives, the relative concentration of two or more deformable additives, the composition of the base fluid, the concentration or range of concentration of one or more additional additives, the composition of one or more additional additives, or any combination thereof. It should be noted that the above parameters being based on the relative pore plugging propensity the samples tested does not imply or limit the development and/or formulation of treatment fluids or treatment fluid additives to be limited to the exact composition of the samples tested. By way of nonlimiting example, a sample may include a deformable additive at a first concentration while the treatment fluid derived therefrom includes the same deformable additive at a second concentration. By way of another nonlimiting example, a series of samples may include two or more deformable additives at various relative concentrations while the treatment fluid additive derived therefrom includes the two or more deformable additives at a relative concentration not tested. By way of another nonlimiting example, a series of samples may include a single deformable additive composition at varying concentrations with varying base fluids (e.g., varying brine compositions) while the treatment fluid derived therefrom includes the deformable additive at a specified concentration and a base fluid in a combination not explicitly tested.

Some embodiments of the present invention may involve performing a subterranean operation with treatment fluids or treatment fluid additives developed and/or formulated based on the relative pore plugging propensity of samples used in conjunction with the present invention, whether the relative pore plugging propensity be based on two or more samples relative to each other or one or more samples relative to a scale. In some embodiments, subterranean operations may be porosity maintaining operations. In some embodiments, subterranean operations may be porosity plugging operations.

Suitable subterranean operations may include, but are not limited to, drilling operations, drill-in operations, lost circulation operations, stimulation operations, sand control operations, completion operations, acidizing operations, scale inhibiting operations, water-blocking operations, clay stabilizer operations, fracturing operations, frac-packing operations, gravel packing operations, wellbore strengthening operations, and sag control operations. Suitable subterranean operations may be used in full-scale operations or pills. As used herein, a "pill" is a type of relatively small volume of specially prepared treatment fluid placed or circulated in the wellbore.

In some embodiments, a method of the present invention may comprise: providing two or more samples each comprising a base fluid and at least one deformable additive; measuring exponential shear values of the samples; and determining a relative pore plugging propensity of the samples relative to each other from the exponential shear values or rheological values derived therefrom. In some embodiments, the rheological values derived from the exponential shear values are at least one selected from the group consisting of strain hardening, strain softening, shear thinning, shear thickening, an extensional viscosity measure, and any combination thereof. In some embodiments, the deformable additive may comprise at least one selected from the group consisting of a polymer, a gelling agent, a viscoelastic surfactant, an emulsion droplet, a liquid crystal, a polymeric microgel, a capsule, a deformable weighting agent, a plasticized polymeric additive, a lost circulation material, a fiber, a carbon nanotube, and any combination thereof. In some embodiments, the deformable additive may comprise a hard particle having a deformable coating. In some embodiments, each sample may comprise a different deformable additive composition that differs in at least one way selected from the group consisting of different deformable additives, different concentrations of the same deformable additives, different relative concentrations of two or more deformable additives, and any combination thereof. In some embodiments, at least one of the samples may further comprise an additional additive. In some embodiments, the method may further comprise developing a treatment fluid additive based on the relative pore plugging propensity of the samples relative to each. In some embodiments, the treatment fluid additive may be for at least one subterranean operation selected from the group consisting of drilling, acidizing, and fracturing. In some embodiments, the treatment fluid additive may be for at least one subterranean operation selected from the group consisting of fluid loss control, wellbore strengthening, and zonal isolation. In some embodiments, the method may further comprise treating at least a portion of a subterranean formation with the treatment fluid additive.

In some embodiments, a method of the present invention may comprise: providing at least two samples each comprising a base fluid and at least one deformable additive, wherein the deformable additive composition of each sample is different; measuring exponential shear values of the samples; determining a relative pore plugging propensity of the samples relative to each other from the exponential shear values or rheological values derived therefrom; and formulating a treatment fluid based on the relative pore plugging propensity of the samples relative to each. In some embodiments, the rheological values derived from the exponential shear values may be at least one selected from the group consisting of strain hardening, strain softening, shear thinning, shear thickening, an extensional viscosity measure, and any combination thereof. In some embodiments, the deformable additive may comprise at least one selected from the group consisting of a polymer, a gelling agent, a viscoelastic surfactant, an emulsion droplet, a lost circulation material, a fiber, a carbon nanotube, and any combination thereof. In some embodiments, the deformable additive composition of each sample may differ in at least one way selected from the group consisting of different deformable additives, different concentrations of the same deformable additives, different relative concentrations of two or more deformable additives, and any combination thereof. In some embodiments, at least one of the samples may further comprise an additional additive. In some embodiments, the treatment fluid may be for a porosity maintaining operation. In some embodiments, the treatment fluid may be for a porosity plugging operation. In some embodiments, the method may further comprise treating at least a portion of a subterranean formation with the treatment fluid additive.

In some embodiments, a method of the present invention may comprise: providing a sample that comprises a base fluid and at least one deformable additive; measuring a strain hardening value for the sample under exponential shear with a strain scale factor of 0.5; and developing a treatment fluid additive based on the strain hardening value relative to a strain hardening scale. In some embodiments, the at least one deformable additive may be different than the treatment fluid additive. In some embodiments, the treatment fluid additive may be for at least one subterranean operation selected from the group consisting of drilling, acidizing, and fracturing. In some embodiments, the treatment fluid additive may be for at least one subterranean operation selected from the group consisting of fluid loss control, wellbore strengthening, and zonal isolation. In some embodiments, the deformable additive may comprise at least one selected from the group consisting of a polymer, a gelling agent, a viscoelastic surfactant, an emulsion droplet, a liquid crystal, a polymeric microgel, a capsule, a deformable weighting agent, a plasticized polymeric additive, a lost circulation material, a fiber, a carbon nanotube, and any combination thereof. In some embodiments, the deformable additive may comprise a hard particle having a deformable coating. In some embodiments, the method may further comprise treating at least a portion of a subterranean formation with the treatment fluid additive.

To facilitate a better understanding of the present invention, the following examples of preferred embodiments are given. In no way should the following representative examples be read to limit, or to define, the scope of the invention.

EXAMPLES

Five samples were tested to determine their relative pore plugging propensity as being relative to each other rather than relative to a scale. The first sample included a branched biopolymer (XANVIS®, xanthan biopolymer, available from Kelco Oil Field Group) in a monovalent brine (9.5 pounds per gallon ("ppg") KCl/NaCl brine) at a concentration of 1.25 pounds per barrel ("lb/bbl") of branched biopolymer in monovalent brine. The second sample included a hyperbranched polymer (EXP-S192™, a polydiallyldimethylammonium chloride polymer, available from Drilling Specialties) in a divalent brine (14.0 ppg $CaCl_2/CaBr_2$ brine) at a concentration of 5 lb/bbl of hyperbranched polymer in divalent brine. The third sample included a linear biopolymer #1 (POLYTRAN-FS™, a nonionic polysaccharide, available from Pillsbury Company) in a divalent brine at a concentration of 3.75 lb/bbl of linear biopolymer #1 in divalent brine. The fourth sample included a linear biopolymer #1 in a monovalent brine at a concentration of 3.75 lb/bbl of linear biopolymer #1 in monovalent brine. The fifth sample included linear biopolymer #2 (HEC-10, hydroxyethyl cellulose, available from DOW Chemical USA) in a divalent brine at a concentration of 2 lb/bbl of linear biopolymer #2 in divalent brine. The exponential shear values were obtained for each fluid at 120° F. with the strain factor held constant at 1 and the exponential rate constant increased from 0.01 to 1. FIGS. 2A-E provide the instantaneous exponential viscosity, $\eta^e$, (a measure of the extensional viscosity) as a function of increasing strain. FIG. 3 provides the instantaneous exponential viscosity, $\eta^e$, for each of the samples tested at a constant exponential rate of $\alpha=0.5$.

First, for the branched biopolymer in a monovalent brine (FIG. 2A) the instantaneous exponential viscosity, $\eta^e$, is observed to initially increase with strain (e.g., the effective pore length over which shear has been experienced) regardless of the value of $\alpha$, the exponential acceleration rate of the shear, used for the test. At a common strain of ~1, the exponential viscosity reaches a peak and begins to decrease with strain. Since strain rate is also increasing with the increasing strain, this is observed as a simple shear-thinning response. However, at higher acceleration rates this shear-thinning behavior slows and $\eta^e$ beings to plateau at high values of strain. This is a strain-hardening effect, where at very high strains the stretching of the polymer chains begins to hinder further flow. From this it can be surmised that the extensional viscosity in the pore is increasing, also due to chain stretching, thus preventing the invasion of the polymer chain into the pore.

For the hyperbranched polymer in a divalent brine (FIG. 2B), the same increase in $\eta^e$ through a strain of ~1 is observed; however, at higher acceleration rates the peak becomes muted and eventually vanishes. Also, for moderate acceleration rates $\eta^e$ tends to collapse onto a single line. Since the shear rate for a particular strain is higher when the acceleration rate is higher, this coalescence of viscosity/strain curves translates to increasing viscosity for a common shear rate. Again, as in the branched biopolymer in a monovalent brine, strain-hardening is observed at the highest acceleration rates.

When considering the linear biopolymer #1 in a divalent brine (FIG. 2C), the same peak in exponential viscosity at low strains as seen in the branched biopolymer in a monovalent brine and hyperbranched polymer in a divalent brine samples is not observed. This is not simply a function of the shear viscosity of the linear biopolymer #1 in a divalent brine, as it is very similar to that of the hyperbranched polymer in a divalent brine, and must be a function of the polymer chain and/or its interaction with the brine. In addition, at high strains shear-thinning continues—even at the highest accelerations rates. No strain-hardening is observed in the linear biopolymer #1 in a divalent brine; at high acceleration rates and high strain, some degree of strain softening is observed. This lack of strain-hardening (e.g., lack of increased resistance of the polymer chains to flow over long distances through the pore) translates into an ability for the linear biopolymer #1 in a divalent brine to penetrate further into the formation, thus increasing interactions of the polymer with the formation (absorption onto the pore walls) and increasing the difficulty of removing the linear polymer from the formation and decreasing the observed regain permeability.

Figure 2A:
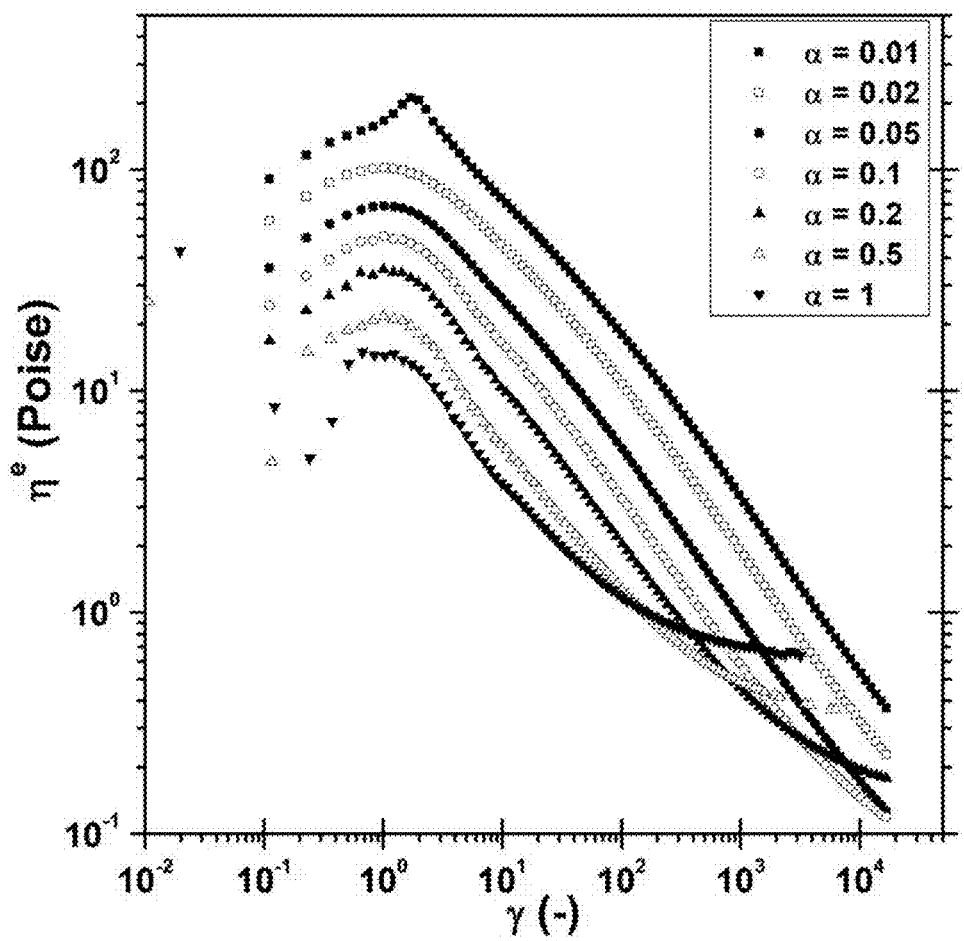
FIGS. 2A-E provide the instantaneous exponential viscosity, $\eta^e$, (a measure of the extensional viscosity) as a function of increasing strain for various samples.
Figure 2B:
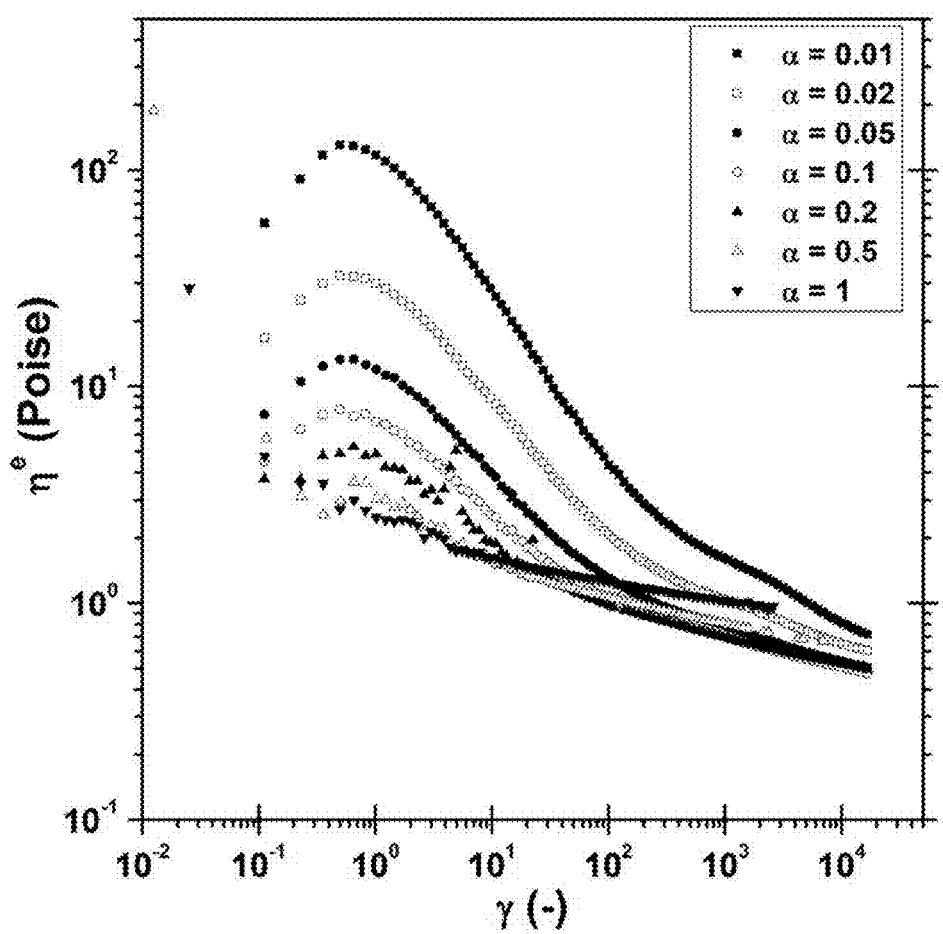
Figure 2C:
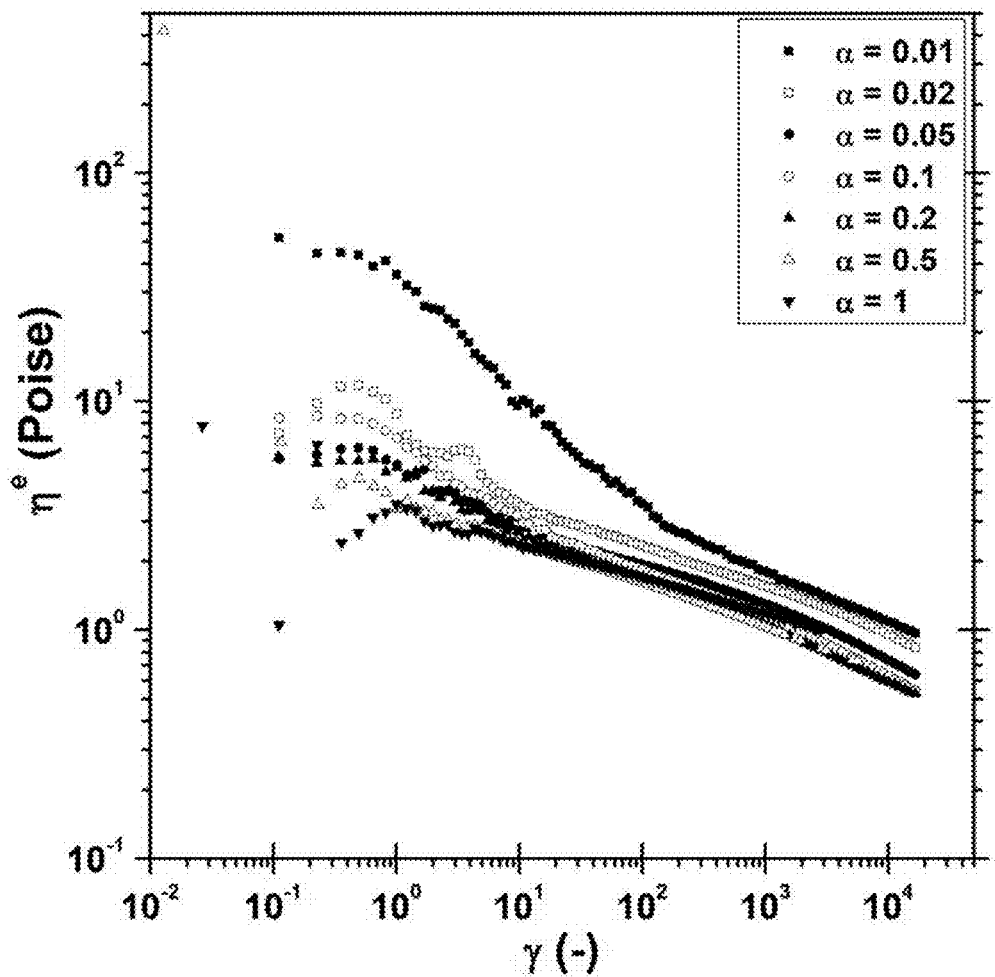
Figure 2D:
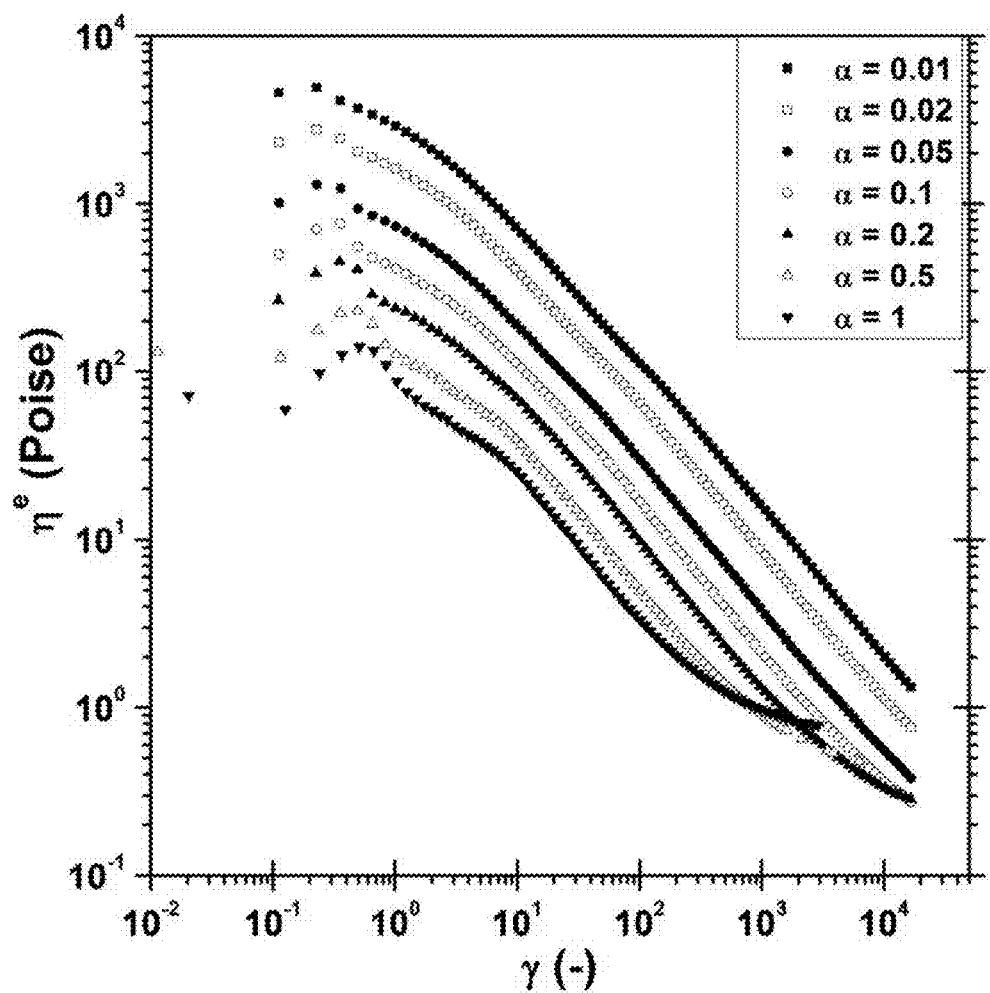
Figure 2E:
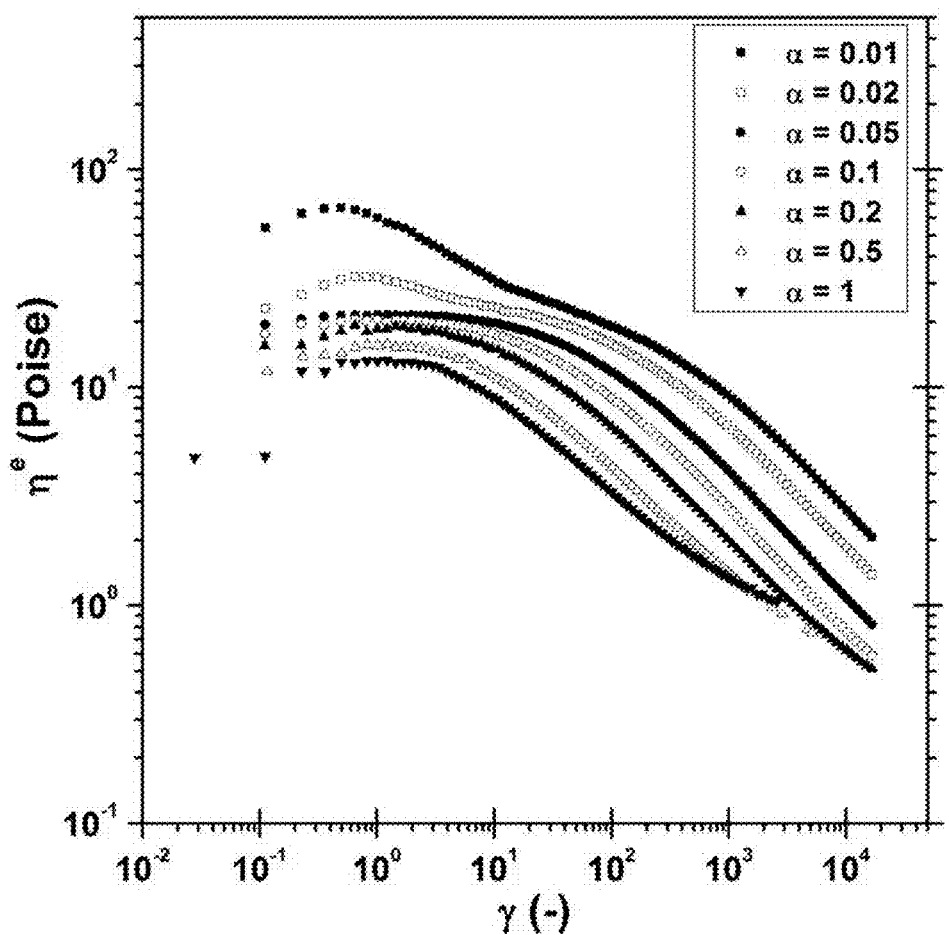
Figure 3:
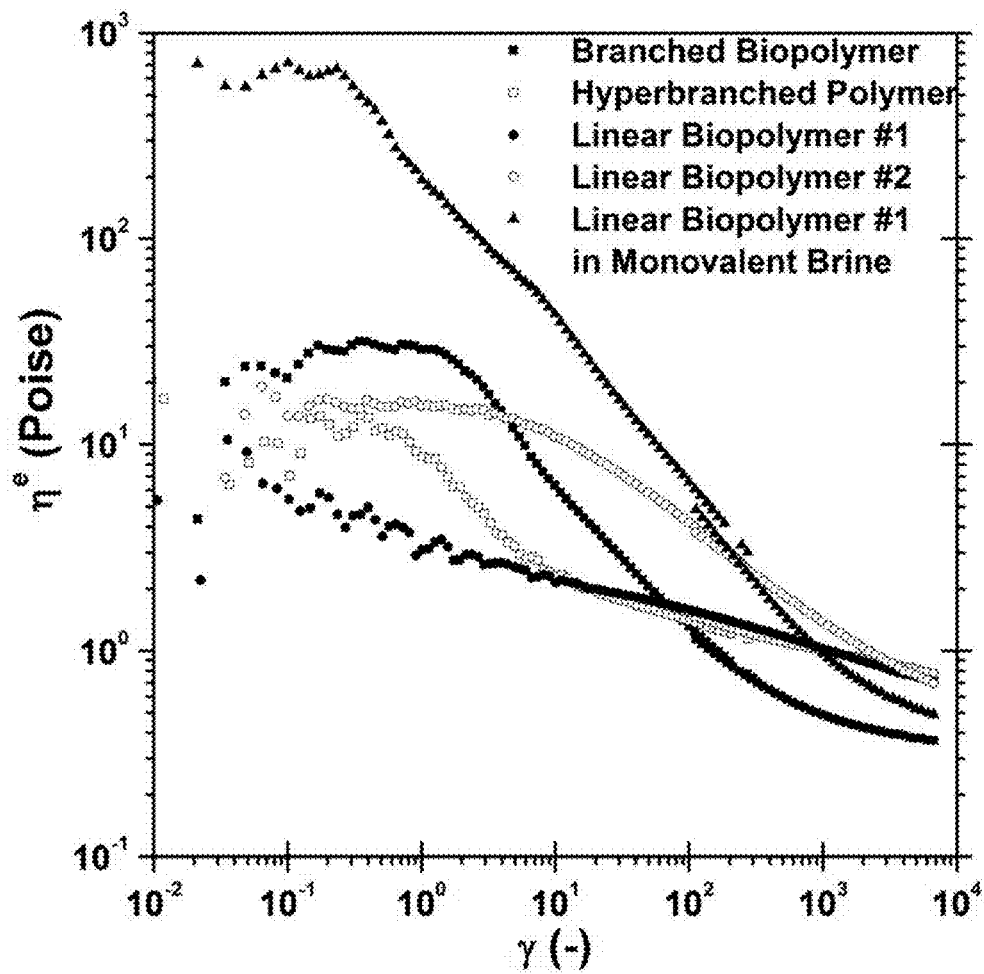
FIG. 3 provides the instantaneous exponential viscosity, $\eta^e$, for each of the samples tested at a constant exponential rate of $\alpha=0.5$.

The exponential shear tests were also conducted on the linear biopolymer #1 in monovalent brine (FIG. 2D). By changing the brine, and thus the charge screening effects on the linear biopolymer #1 chain, the rheological properties of the fluid were dramatically changed. Unlike when tested in divalent brine, the linear biopolymer #1 in monovalent brine exhibits exponential shear results very similar in form as the branched biopolymer in monovalent brine. A defined exponential viscosity peak is observed at a strain of ~1, as well as the onset of a plateau in $\eta^e$ at high strain and high acceleration rates. However, the degree of strain-hardening observed is not as great as in the branched biopolymer in a monovalent brine or hyperbranched polymer in a divalent brine.

By comparison, linear biopolymer #2 exhibits several similarities in exponential shear tests to linear biopolymer #1. While the data at different acceleration rates does not quite collapse onto a single curve as in linear biopolymer #1, there is the same consistent shear-thinning at high strains. At the highest acceleration rates, at very high strains, there is a small positive inflection indicating some strain hardening, but not nearly to the degree observed in the branched and hyperbranched polymer fluids.

A comparison of the instantaneous exponential viscosity for the five samples, at a common acceleration rate of $\alpha=0.5$ is presented in FIG. 3. From this a basis for modeling the formation damage from exponential shear tests can be begun. These curves were produced at two different values of the strain scale factor, with A=0.1 and A=10, the results of which overlapped well to produce a single continuous curve. The previously noted appearance of strain hardening in the branched and hyperbranched polymer fluids is again evident, with the hyperbranched polymer fluid showing a positive inflecting indicating strain hardening at lower strain ($\gamma=\sim6$) than any other fluid. The branched biopolymer fluid shows inflection at a strain of $\gamma=\sim200$. Both of these also exhibit increased stiffness at very high strains. Linear biopolymer #1 never exhibits a positive inflection indicating strain hardening; instead, at the highest strains a negative inflection is observed indicating some degree of strain softening.

Therefore, the relative pore plugging propensity of the four samples is hyperbranched polymer in a divalent brine<branched biopolymer in a monovalent brine<linear biopolymer #1 in monovalent brine<linear biopolymer #2<linear biopolymer #1 in a divalent brine.

Further, the hyperbranched polymer in a divalent brine, branched biopolymer in a monovalent brine, and linear biopolymer #1 in a divalent brine samples were tested via traditional regain permeability methods with an Automated Return Permeability (ARP) instrument with ~100 mD Berea sandstone cores.

The traditional regain permeability tests were conducted with cores having a 1.5" diameter and >2" length. The cores were dried for >16 hours in an oven at 215° F. The dimensions of the dry cores were measured. The cores were then exposed to 5 wt % NaCl in water under vacuum for 2 hours and soaked for >16 hours in 5 wt % NaCl in water. The weight of the saturated core was then measured. Finally, the pore volume of the cores was calculated based on dry/saturated weights.

The saturated cores were then loaded into the ARP, the confining pressure was raised to 1000 psi with a temperature of 200° F. Then, SOLTROL® (isoparaffin solvent, available from Chevron Phillips Chemical Company) at 4 mL/min was flowed until the permeability was stable, which was recorded as the initial permeability. The sample of interest was then run through the core with 50 psi of differential pressure for 2 pore volumes using dynamic filtration. Finally, SOLTROL® at 4 mL/min was again flowed until permeability was stable, which was recorded as the damage permeability. The permeability difference between the initial permeability and the damage permeability was calculated to be the regain permeability.

The hyperbranched polymer in a divalent brine had ~55% regain permeability. The branched biopolymer in a monovalent brine had ~35% regain permeability. The linear biopolymer #1 in a divalent brine had ~25% regain permeability. These values provide for regain permeabilities of hyperbranched polymer in a divalent brine>branched biopolymer in a monovalent brine>linear biopolymer #1 in a divalent brine, which tracks the relative pore plugging propensity as determined from the strain hardening of the samples.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method comprising:
providing a plurality of samples that comprises a base fluid and at least one deformable additive, the at least one deformable additive being at different concentrations in the plurality of samples;
measuring a strain ($\gamma$) for the plurality of samples under exponential shear with a strain scale factor of 0.5; and
plotting an exponential viscosity curve of an instantaneous exponential viscosity ($\eta^e$) as a function of the strain for each of the plurality of samples; and
producing a treatment fluid additive for at least one subterranean operation selected from the group consisting of fluid loss control, wellbore strengthening, and zonal isolation, wherein the treatment fluid additive comprises the at least one deformable additive in a sample selected from the one or more samples that has a positive inflection point on the exponential viscosity curve at a strain of 500 or greater.

2. The method of claim 1 further comprising:
treating at least a portion of a subterranean formation with a treatment fluid comprising the treatment fluid additive.

3. The method of claim 2, wherein the treatment fluid additive is present in the treatment fluid at up to 25% by volume of the treatment fluid.

4. The method of claim 1, wherein the different concentrations of the at least one deformable additive in the plurality of samples ranges from 0.001% to 75% by volume of the base fluid.

5. A method comprising:
providing a plurality of samples that comprises a base fluid and at least one deformable additive, the at least one deformable additive being at different concentrations in the plurality of samples;
measuring a strain ($\gamma$) for the plurality of samples under exponential shear with a strain scale factor of 0.5;
plotting an exponential viscosity curve of an instantaneous exponential viscosity ($\eta^e$) as a function of the strain for each of the plurality of samples; and
producing a treatment fluid additive for at least one subterranean operation selected from the group consisting of drilling, acidizing, and fracturing, wherein the treatment fluid additive comprises the at least one deformable additive in a sample selected from the one or more samples that has a positive inflection point on the exponential viscosity curve at a strain of less than 200.

6. The method of claim 5 further comprising:
treating at least a portion of a subterranean formation with a treatment fluid comprising the treatment fluid additive.

7. The method of claim 6, wherein the treatment fluid additive is present in the treatment fluid at up to 25% by volume of the treatment fluid.

8. The method of claim 5, wherein the different concentrations of the at least one deformable additive in the plurality of samples ranges from 0.001% to 75% by volume of the base fluid.

* * * * *